United States Patent
Frankinet

(10) Patent No.: US 7,872,753 B2
(45) Date of Patent: Jan. 18, 2011

(54) METHOD AND APPARATUS FOR ESTABLISHING REFLECTION PROPERTIES OF A SURFACE

(75) Inventor: Marc Frankinet, Horion-Hozemont (BE)

(73) Assignee: Schreder, Brussels (BE)

( * ) Notice: Subject to any disclaimer, the term of this patent is extended or adjusted under 35 U.S.C. 154(b) by 103 days.

(21) Appl. No.: 12/093,820

(22) PCT Filed: Nov. 22, 2006

(86) PCT No.: PCT/EP2006/068770

§ 371 (c)(1),
(2), (4) Date: Aug. 25, 2008

(87) PCT Pub. No.: WO2007/060181

PCT Pub. Date: May 31, 2007

(65) Prior Publication Data

US 2008/0309942 A1    Dec. 18, 2008

(30) Foreign Application Priority Data

Nov. 24, 2005  (BE) ................................. 2005/0575
Nov. 24, 2005  (EP) ................................. 05111207
Apr. 10, 2006  (EP) ................................. 06112416

(51) Int. Cl.
   G01N 21/55    (2006.01)
   G01J 1/58     (2006.01)
(52) U.S. Cl. ..................... 356/445; 356/448; 250/458.1
(58) Field of Classification Search ......... 356/445–448, 356/600–603, 392–398; 250/458.1–461.1
   See application file for complete search history.

(56) References Cited

U.S. PATENT DOCUMENTS 4,917,495 A  *  4/1990  Steenhoek ................... 356/328

(Continued)

FOREIGN PATENT DOCUMENTS

EP     1550381 A1    7/2005

(Continued)

OTHER PUBLICATIONS

Bommel et al.; Road Surfaces and Lighting; Joint Technical Report CIE/PIARC; 1984; pp. 16-21, 45-53 and 62-6; vol. 664.

(Continued)

*Primary Examiner*—Sang Nguyen
(74) *Attorney, Agent, or Firm*—Charles L. Warner, II; Jason A. Bernstein; Bryan Cave LLP

(57) ABSTRACT

A method for establishing light reflection properties of a specific surface, by measuring, for a plurality of comparison surfaces, the r-tables in accordance with CIE standard recommendations, measuring, for the same plurality of comparison surfaces, a light reflection parameter for selected angles ($\gamma$) of incident light and angles (90°–$\alpha$) and ($\beta$) of reflected light, using a 'portable' measuring apparatus, measuring in situ, on multiple measuring points of said specific surface, said parameter for said angles ($\gamma$), ($\alpha$) and ($\beta$), using said 'portable' apparatus, comparing the angular distribution of said parameter for the specific surface with that for said comparison surfaces, to select the comparison surface showing the best distribution fit, optionally taking into account a rescaling factor on luminance coefficient Q0, and assigning to said specific surface the 'r-table' corresponding to said selected comparison surface, with said optional rescaling factor.

8 Claims, 9 Drawing Sheets

U.S. PATENT DOCUMENTS

| | | | | |
|---|---|---|---|---|
| 5,387,977 A | * | 2/1995 | Berg et al. | 356/407 |
| 5,640,244 A | | 6/1997 | Hellstrom et al. | |
| 5,691,817 A | * | 11/1997 | Cargill et al. | 356/405 |
| 6,233,053 B1 | * | 5/2001 | Preston et al. | 356/445 |
| 6,473,165 B1 | * | 10/2002 | Coombs et al. | 356/71 |
| 6,631,000 B1 | * | 10/2003 | Schwarz | 356/445 |
| 6,825,484 B2 | * | 11/2004 | Burkatovsky | 250/559.18 |
| 7,019,826 B2 | * | 3/2006 | Vook et al. | 356/237.1 |
| 7,667,856 B2 | * | 2/2010 | Fukamizu et al. | 356/614 |

FOREIGN PATENT DOCUMENTS

| | | |
|---|---|---|
| FR | 2618543 A1 | 1/1989 |
| WO | 2004095007 A1 | 11/2004 |

OTHER PUBLICATIONS

Calculation and Measurement of Luminance and Illuminance in Road Lighting; CIE Journal, Commission Internationale de l'Eclairage; 1982; pp. 1-159; Paris, France.

Search Report for International Patent Application No. PCT/EP2006/068770; Mar. 6, 2007.

* cited by examiner

Principles of comparison method

Sorted according to decreasing similarity

| | Fact | Chi² | S1 | Description |
|---|---|---|---|---|
| 18 | 1 | 0 | 0.721 | site 9_1 |
| 19 | 1 | 22 | 0.732 | site9_2 |
| 4 | 0.9 | 31 | 0.558 | site4_4 |
| 20 | 1 | 58 | 0.735 | site9_3 |
| 7 | 0.7 | 81 | 0.641 | site4_2 |
| 8 | 0.9 | 86 | 0.674 | site4_3 |
| 6 | 0.7 | 106 | 0.622 | site4_2 |
| 9 | 0.9 | 131 | 0.568 | site5_1 |
| 10 | 0.9 | 142 | 0.59 | site5_2 |
| 5 | 0.7 | 168 | 0.597 | site4_1 |
| 15 | 1.5 | 343 | 0.586 | site7_2 |
| 14 | 1.6 | 545 | 0.782 | site7_1 |
| 3 | 0.8 | 2348 | 0.874 | site3_2 |
| 2 | 0.8 | 2383 | 0.868 | site3_3 |
| 17 | 0.4 | 2510 | 0.258 | site8_1 |
| 1 | 0.9 | 2650 | 0.899 | site3_1 |
| 13 | 0.5 | 4546 | 0.135 | site6_2 |
| 16 | 0.7 | 4559 | 0.248 | site8_2 |
| 12 | 0.5 | 4654 | 0.136 | site6_2 |
| 11 | 0.5 | 4794 | 0.121 | site6_1 |

*Fig. 6a*

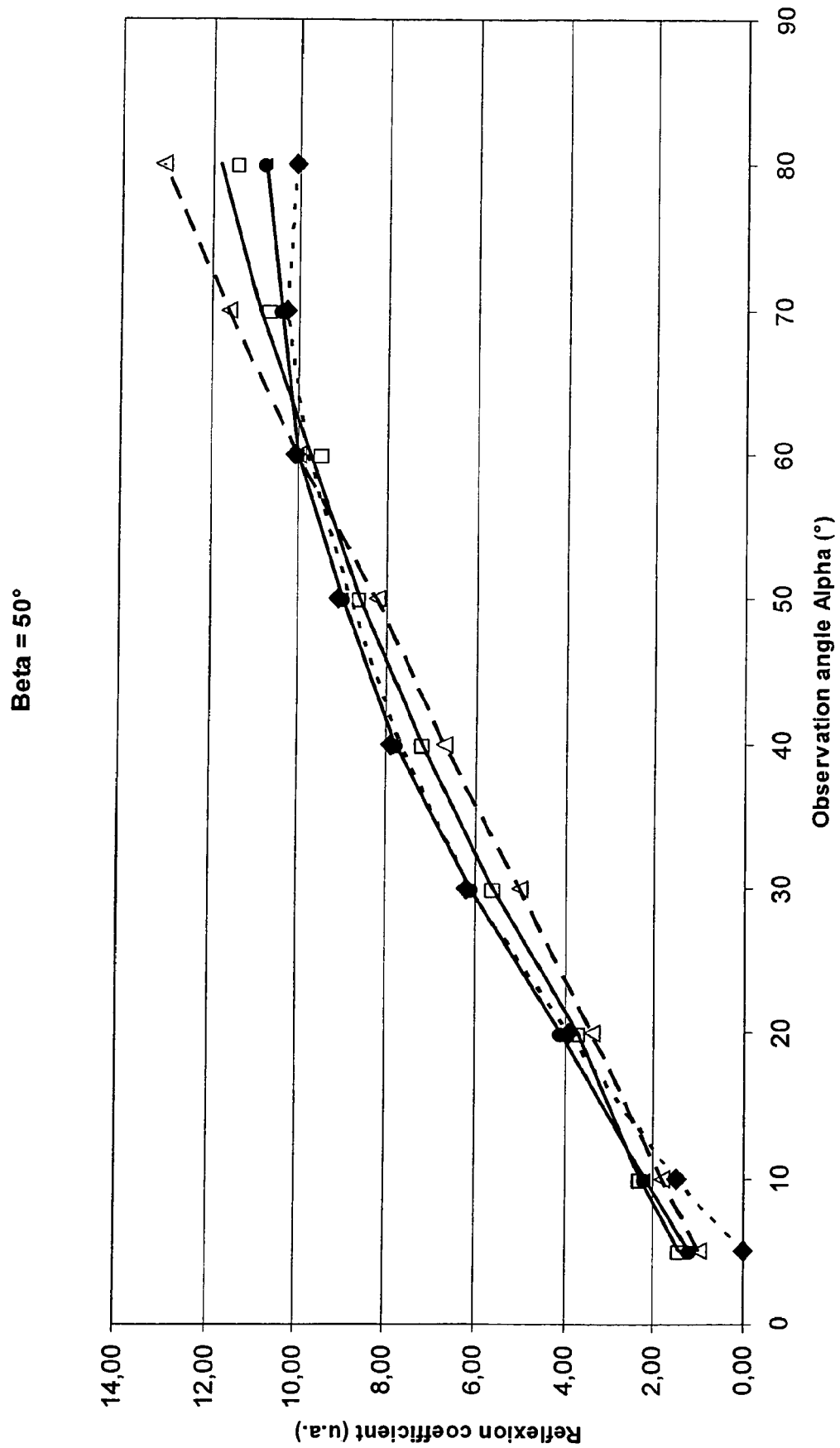

METHOD AND APPARATUS FOR ESTABLISHING REFLECTION PROPERTIES OF A SURFACE

CROSS-REFERENCE TO RELATED APPLICATIONS

This patent application is a U.S. National Phase of International Patent Application No. PCT/EP2006/068770, filed Nov. 22, 2006, which claims priority to Belgian Patent Application No. 2005/0575, filed Nov. 24, 2005; European Patent Application No. 05111207.6, filed Nov. 24, 2005; and European Patent Application No. 06112416.0, filed Apr. 10, 2006, the disclosures of which are incorporated herein by reference in their entirety.

BACKGROUND OF THE INVENTION (1) Field of the Invention

The invention relates to a method for establishing (=determining, finding, "measuring") reflection properties of a given surface, such as a road surface, among others in view of deducing there from the desired illuminance and luminance performances of lighting systems/installations.

The invention more particularly aims at deducing a series of representative parameters of an unknown surface, such as those collectively referred to as "r-table" or "table-r", specifically representative of the light reflection or reflectance of a road surface, from the measurement, in situ, of converted luminance parameters of said road surface/road covering. at defined angles of the light incidence and of the light reflection.

(2) Description of Related Art

Determination of the reflection properties of a road surface is an important aspect for calculating the characteristics and the luminance level of road lighting installations. Particular reference is made in this respect to the publication "Calculation and Measurement of Luminance and Illuminance in road lighting" from the Commission Internationale de l'Eclairage—CIE (Publication CIE No. 30-2 (TC-4.6) 1982) the entire content of which is incorporated by reference in the present text. In order to design a lighting installation and optimise it in respect of luminance, lighting engineers must be able to predict the luminance levels at the road surface. Several parameters have to be taken into account for that purpose: the intensity distribution of the emitted light which in general is quite well known and defined by the manufacturers of lighting apparatuses; the light flux of the lamps, the geometry of the configuration (width of the road, height of the installation, etc.) and the properties of the road surface.

Luminance calculations are often performed by means of software and more in general by using theoretical road surface characteristics, such as the r-table characteristics defined by the CIE.

Calculations for lighting installations are often based on the characteristics of a very limited number of reference surfaces (such as standard classes R1, R2, R3 and R4 as defined by CIE).

The use of such a limited number of reference surfaces for characterising all imaginable road surfaces clearly suggest that improvements to the method are desirable.

The conceiver of the present invention was one of the pioneers in this area and carried out numerous measurements of road surface properties using a rather sophisticated gonio-reflectometer. This instrument is capable of measuring the behaviour of a road surface both at an observation angle of 1° ($\alpha=1°$, i.e. the specific viewing angle of a car driver) and at other observation angles ($\alpha$ up to 90°), more appropriate for measuring the characteristics of, for instance, tunnel walls. For carrying out such measurements, it is necessary to extract samples (having a cross section of 100 $mm^2$ to 200 $mm^2$) from the road surface, in order to subsequently measure those in the laboratory where the gonio-reflectometer is installed.

The thus obtained "r-table" characteristics, representing the behaviour of the road surface at a given observation angle (1° for road lighting applications) can then be introduced in appropriate software programmes (well known per se to those skilled in the art) so that luminance of the lighting installations can be predicted with good accuracy. The extraction of road samples is traffic disturbing, time consuming and costly so that in general no more than 2-3 samples are taken and analysed.

The essential question remains however whether a few (2-3) samples may really be representative of the entire surface of a road, knowing that such a road is never quite homogeneous. The answer is clearly "no".

Therefore the calculated luminance will not really be representative of the actual situation.

A solution to improve this situation would involve taking and analysing more samples, and to perform calculations on the basis of average values, but this has proven too expensive.

BRIEF SUMMARY OF THE INVENTION

It is the objective of the invention to solve the problems referred to above.

To achieve this the invention takes the approach of using use a "portable" (easily movable/transportable) equipment ("portable gonio-reflectometer"). The results obtained with such a portable equipment are less accurate than those obtained with a laboratory type gonio-reflectometer, but owing to the fact that it is much easier to make multiple measurements the global result can nevertheless be more representative.

It is a further objective of the invention to develop a method in which r-table of a specific surface to be measured (hereafter referred to as a "specific surface") is established/determined/ deducted by comparison with r-tables of existing/known surfaces (hereafter referred to as "comparison surface"), rather than by actually measuring the r-table using a laboratory type gonio-reflectometer.

It is still a further objective of the invention to develop a measurement that avoids making measures at an angle of 1°, which is impossible, in practice, under conditions other than in cumbersome laboratory situations.

To achieve these objectives the invention provides a method for establishing the light reflection properties of a specific surface by selecting from among a number of "tables of reduced luminance coefficients" ("r-tables") measured for comparison surfaces, a table suited to characterise said specific surface, which method comprises measuring, for samples of a plurality of comparison surfaces, the parameters for their r-tables, using a measuring apparatus in accordance with CIE standard recommendations, measuring, for those same samples of a plurality of comparison surfaces, a selected light reflection parameter for a selected combination of angles ($\gamma$) of incident light and angles ($\alpha$) and ($\beta$) of reflected light, using a "portable" measuring apparatus, measuring in situ, on multiple measuring points of said specific surface, said selected light reflection parameter for said selected combination of angles ($\gamma$) of incident light and angles ($\alpha$) and ($\beta$) of reflected light, using said "portable" apparatus, comparing, by mathematical and/or graphical analysis, the angular distribution of said selected parameter for the specific surface with the angular distribution of said selected parameter for said comparison surfaces, in order to select the comparison surface showing the best distribution fit, optionally taking into account a resealing factor on luminance coefficient Q0, and assigning to said specific surface the light reflection properties of the "r-table" corresponding to said selected comparison surface, with use of said optional resealing factor.

It should be observed in this context, that the principle of portable installations for measuring light reflection properties of road surfaces is know per se in the art and that it is certainly not the object of the present text to claim the principle of such a portable apparatus as such.

International patent publication WO 2004/095007 thus discloses a movable apparatus for measuring and recording reflectance of a road surface. The apparatus comprises a data recording system, a number of light sources emitting toward the road surface, a number of light reflectance detectors and a luminance data recording system. The apparatus can be used on a moving vehicle to measure and record key luminance parameters, to determine compliance with specified light standards for roads.

U.S. Pat. No. 5,640,244 on the other hand discloses an optical scanner for determining characteristics of a surface, comprising at least three light sources directing light to a region of said surface, spaced from one another around said region, and a number of reflective light sensors positioned above said region of the surface and on either side of and spaced apart from a plane along the axis of the light sources, perpendicular to said surface. The scanner is designed for measuring the fibre orientation of a non-woven web.

The methods disclosed in WO 2004/095007 and U.S. Pat. No. 5,640,244 do not suggest comparing the obtained data with standard tables in order to select a most closely corresponding table and obtain optimal accuracy for the method, nor do these prior art methods provide proper data for calculating the requirements of lighting installations.

The concept of the resealing factor to be, optionally, applied in accordance with the present invention, on average luminance coefficient Q0 referred to in the r-table method as recommended by CIE (see disclosure CIE No. 30-2-TC-4.6 as referred to above), is to be understood in the following manner:

Following CIE No. 30-2, if two road surfaces have the same type of light reflection properties, but one being darker than the other, they can have the same "r-table" being just multiplied by a different coefficient Q0 which in fact is a lightness coefficient.

According to a preferred feature of the invention, the method involves carrying out at least 60 measurements each measured sample/each measuring point, to establish said angular distribution of said selected parameter, involving at least 2 selected angles ($\gamma$), at least 5 selected angles ($\alpha$) and at least 2 selected angles ($\beta$).

Most preferably the method involves 180 measurements, for 4 selected angles ($\gamma$), for 9 selected angles ($\alpha$) and for 5 selected angles ($\beta$).

In a preferred embodiment of the invention, the method involves that said 180 measurements are carried out for angles ($\gamma$) selected substantially at a 0°, 30°, 50° and 70°, angles (90°−$\alpha$) selected substantially at a 5°, 10°, 20°, 30°, 40°, 50°, 60°, 70° and 80°, and angles ($\beta$) selected substantially at a 0°, 10°, 20°, 30° and 150°.

According to a further preferred feature of the invention, the mathematical comparative analysis of the angular distribution of said selected parameter for the specific surface with the angular distribution of said selected parameter for said comparison surfaces, as referred to here above, involves a "least squares" analysis method, as it is well known per se for comparing distributions/curves of measuring points.

According to still a further preferred feature of the invention, the "measured light reflection parameter", as referred more above, is the measured luminance (L) divided by the measured illuminance (E) (referred to as the relative reflection parameter L/E), whereas said comparative analysis of said angular distributions compares the distributions of L/E in function of angle ($\gamma$), angle ($\alpha$) and angle ($\beta$) respectively.

Whereas, as stated above, it is not the object of the present invention to claim, as such, the principle of a portable apparatus for measuring light reflection parameters, the invention does actually relate to a portable apparatus for measuring light reflection parameters, comprising a number of light sources emitting towards the same region of a surface to be measured, a number of reflective light sensors positioned above said region and on either side of and spaced apart from a plane along the axis of said light sources perpendicular to said surface, for use in a method according to the invention.

The invention thus specifically relates to such a portable measurement apparatus comprising:

at least three light sources directed towards said region of the surface to be measured, according to different angles ($\gamma$), at least two sets of luminance-calibrated photovoltaic cells with support tubes for collimating the reflected light, whereas each cell of one set is directed, with its collimating support tube, towards said region of the surface to be measured, according to different angles ($\alpha$), and whereas said at least two sets of cells each lie in different planes perpendicular to said surface to be measured, according to angles ($\beta$), at least one additional photovoltaic cell per light source, for the self-calibration thereof In a preferred embodiment of the portable measurement apparatus according to the invention, the apparatus comprises four light sources positioned in one plane perpendicular to said surface to be measured, each source respectively directed according to angles ($\gamma$) of substantially 0°, 30°, 50° and 70°, and provided with optical systems to illuminate the same circular region of the surface to be measured, having a diameter between 5 and 15 cm, preferably between 100 an 125 mm, at a illuminance level above 5000 lux, preferably above 15000 lux.

The thus defined apparatus may most preferably comprise five sets of cells, each set being perpendicular to said surface to be measured and directed according to angles ($\beta$) substantially at 0°, 10°, 20°, 30° and 150° respectively with respect to said plane comprising said light sources, and in that each set comprises nine cells directed according to angles (90°−$\alpha$) substantially at 5°, 10°, 20°, 30°, 40°, 50°, 60°, 70° and 80° respectively with respect to a plane perpendicular to said surface to be measured.

The method according to the invention is particularly useful as part of calculation methods of lighting installations for roads and/or road constructions involving experimental and/or theoretical lighting characteristics for said roads/road constructions, and therefore specifically relates to any calculation method, optionally using specific software, in which the used experimental/theoretical lighting characteristics for the road/road construction comprise light reflection properties obtained through a method according to the invention or by means of an apparatus according to the invention.

The invention finally also relates to any software designed to implement a method according to the invention and/or to operate/assist an apparatus according to the invention.

In particular the invention thus also relates to any software assisted, comparative analysis of light reflection properties of road surfaces, so as to generate parameters necessary for the calculation of lighting installations, in which light reflection properties of a specific surface are established by selecting from among a number of "tables of reduced luminance coefficients" ("r-tables") measured for comparison surfaces, a table suited to characterise said specific surface, by measuring, for samples of a plurality of comparison surfaces, the parameters for their r-tables, using a measuring apparatus in accordance with CIE standard recommendations, measuring, for those same samples of a plurality of comparison surfaces, a selected light reflection parameter for a selected combination of angles ($\gamma$) of incident light and angles ($\alpha$) and ($\beta$) of reflected light, using a "portable" measuring apparatus, measuring in situ, on multiple measuring points of said specific surface, said selected light reflection parameter for said selected combination of angles ($\gamma$) of incident light and angles ($\alpha$) and ($\beta$) of reflected light, using said "portable" apparatus, comparing, by mathematical and/or graphical analysis, the angular distribution of said selected parameter for the specific surface with the angular distribution of said selected parameter for said comparison surfaces, in order to select the comparison surface showing the best distribution fit, optionally taking into account a resealing factor on luminance coefficient Q0, and assigning to said specific surface the light reflection properties of the "r-table" corresponding to said selected comparison surface, with use of said optional resealing factor.

BRIEF DESCRIPTION OF THE DRAWING

Further features and details of the invention will be understood from the following disclosure on practical aspects of the invention and from the attached drawings, in which.

DETAILED DESCRIPTION OF THE INVENTION

Figure 1:
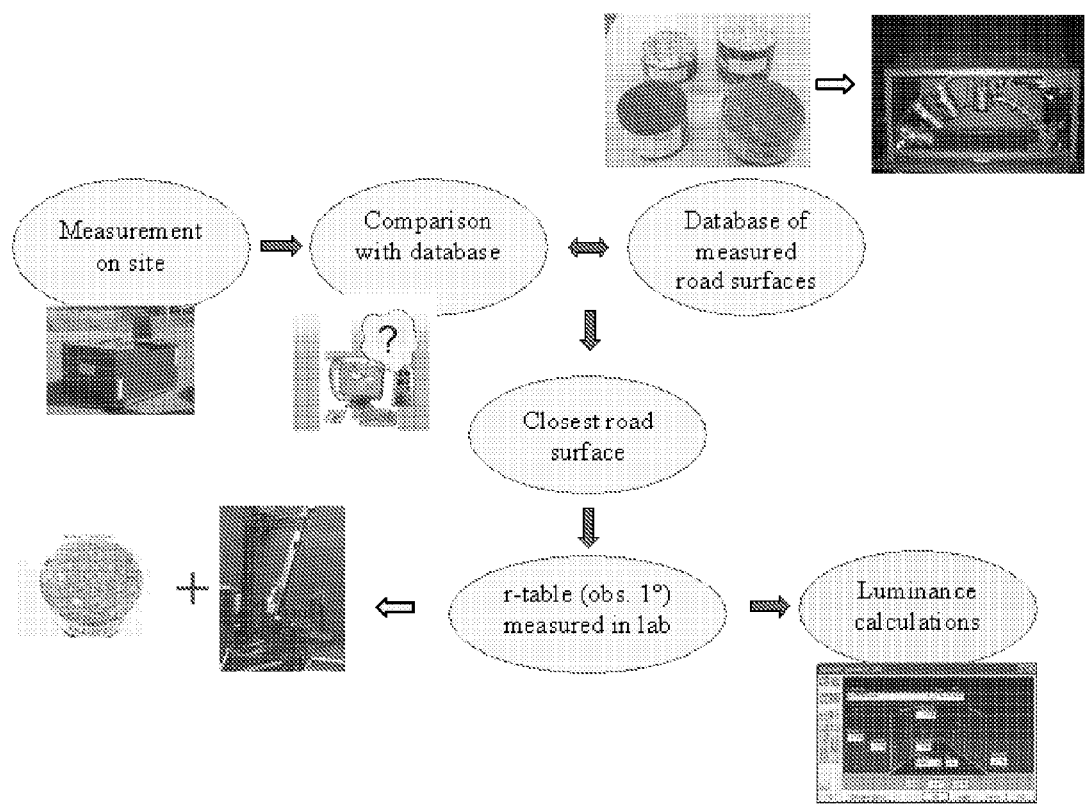
FIG. 1 summarises the principle of the method according to the invention.
Figure 2:
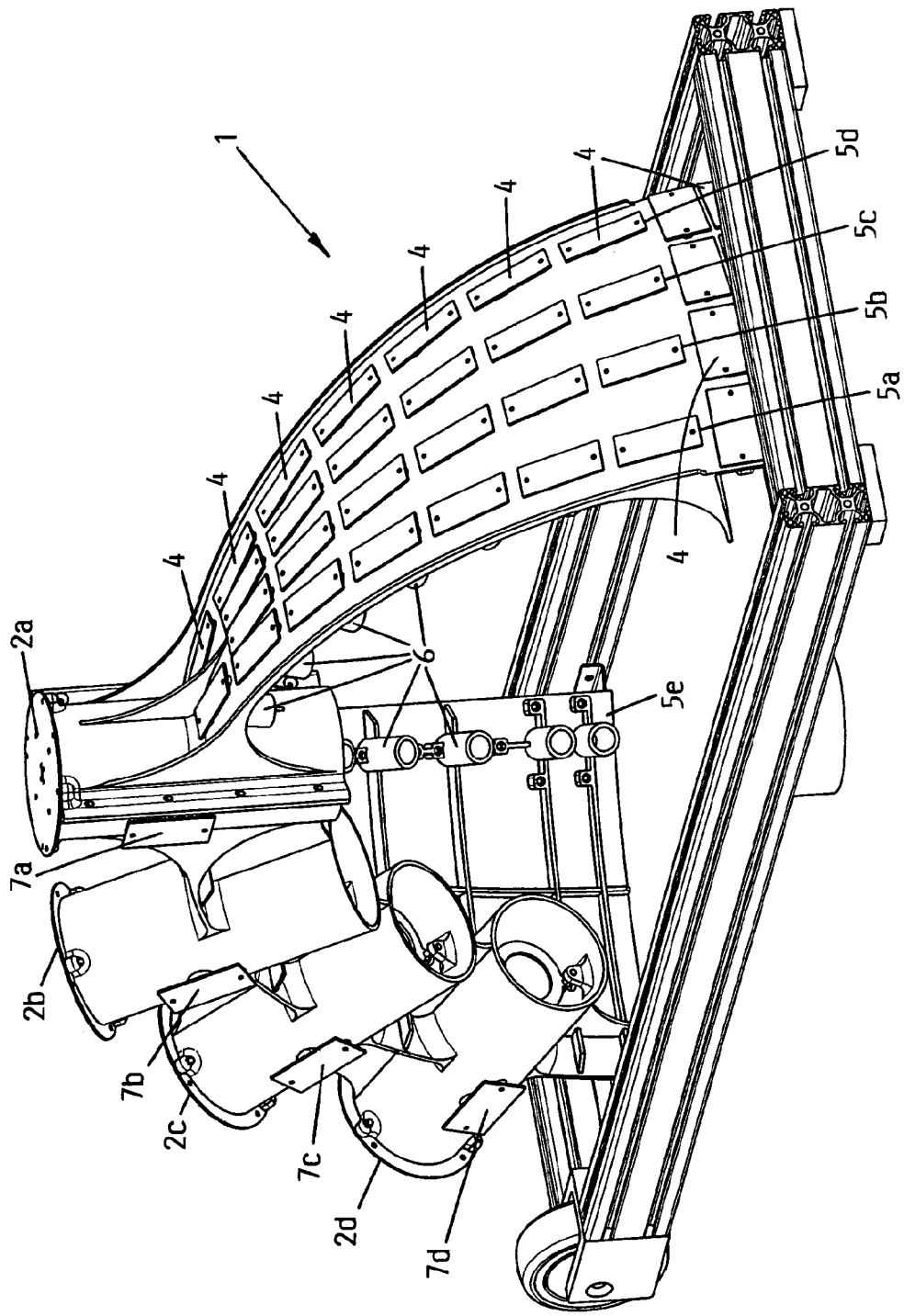
FIGS. 2 and 3 are schematic representations of a portable measurement apparatus in accordance with the invention, viewed from two different angles.
Figure 3:
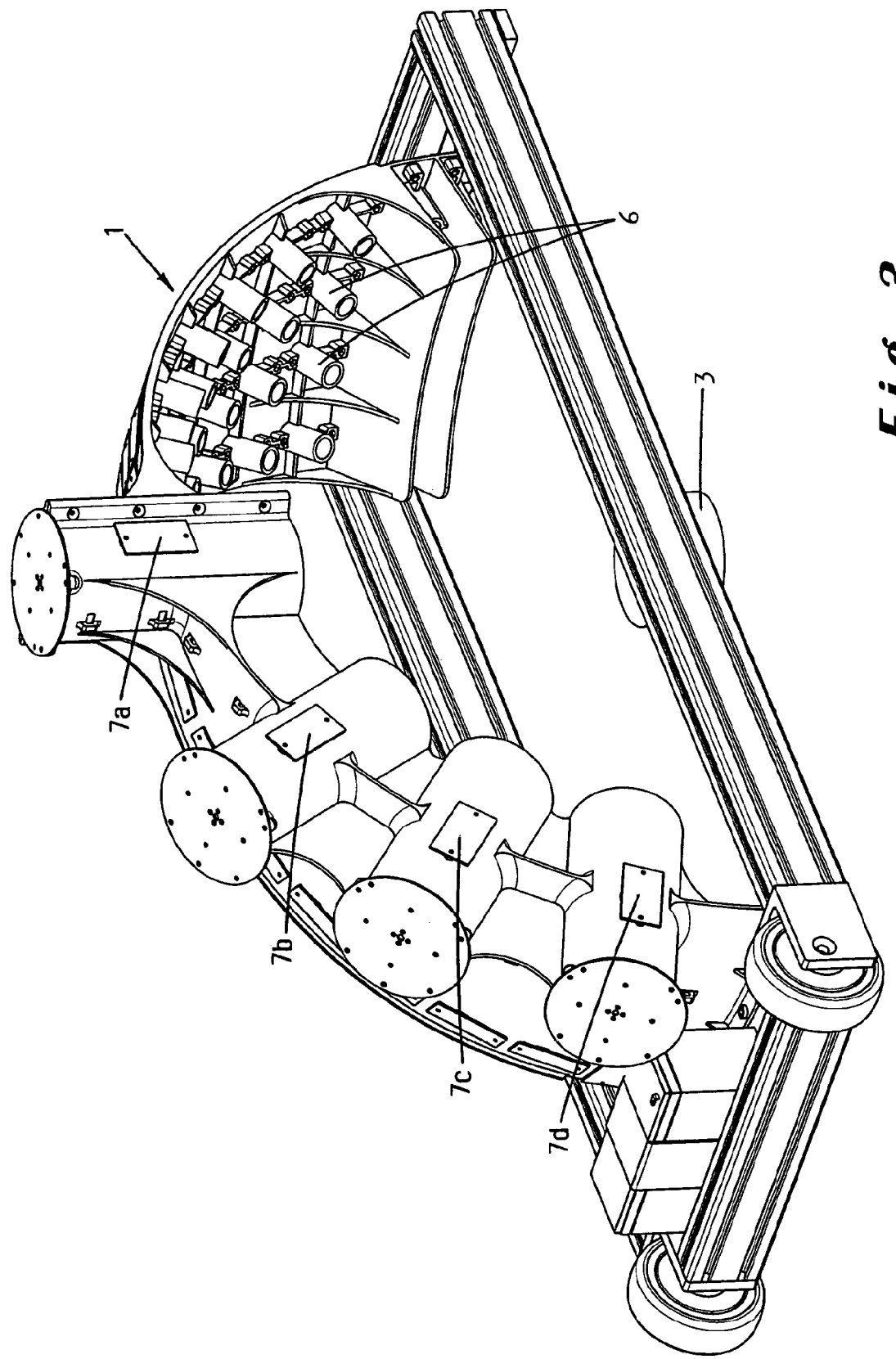
Figure 4:
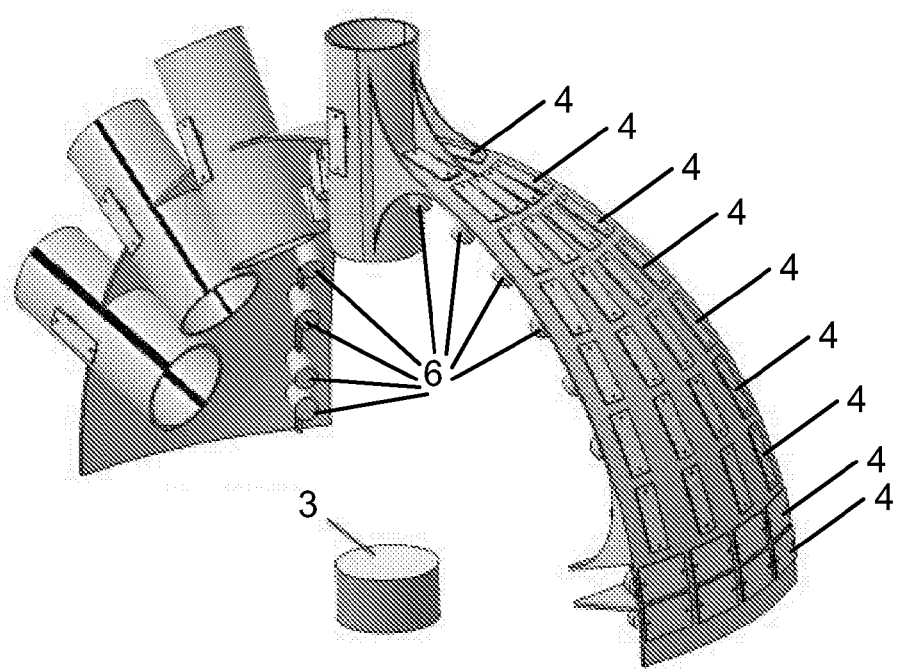
FIGS. 4 and 5 illustrate the functioning of the apparatus and method in accordance with the invention.
Figure 5:
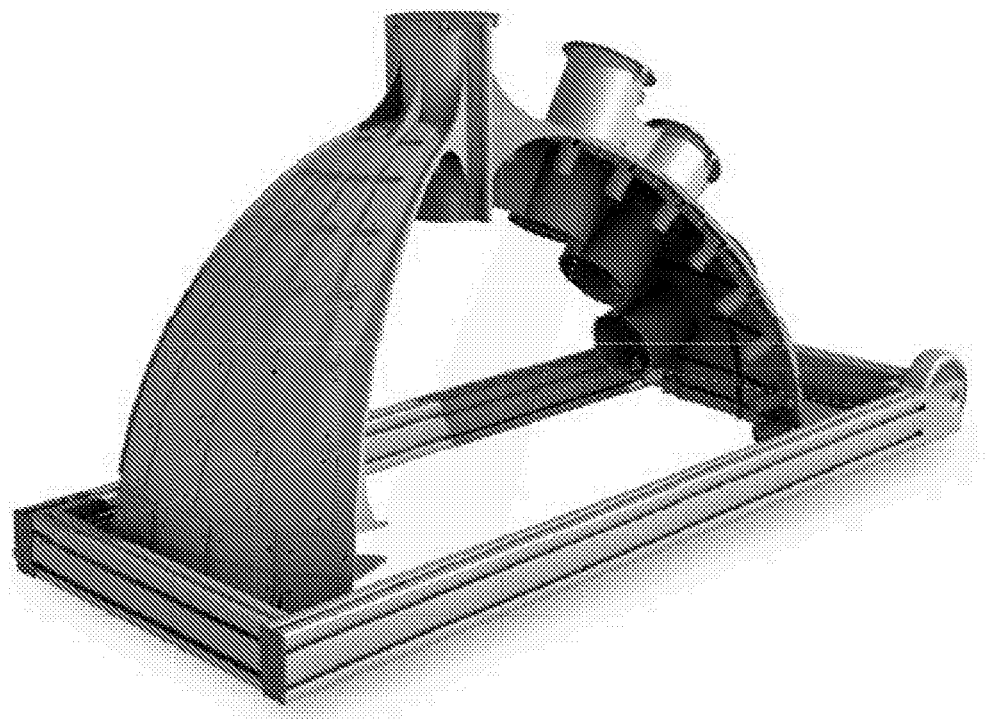

The apparatus (designated with reference numeral 1) shown in FIGS. 1-4 comprises:

four light sources (50 W), designated with reference numerals 2a, 2b, 2c and 2d, equipped with adapted lens systems and positioned according four incident angles of 0°, 30°, 50° and 70°, respectively, in order to illuminate a circular area 3 (having a diameter of 113 mm) on the ground level with a very high uniformity level. The same area is lit whatever the light source. The illuminance level is higher than 15000 lux.

45 photovoltaic light-cells 4, distributed over five sets 5 of nine cells each, each equipped with a little tube 6 ("collimating tube"), and optionally directional "louvers", for the measurement of the reflected light. These photovoltaic light cells 4 with the tubes 6 are calibrated in luminance;

the light cells are distributed over the five sets 5a, 5b, 5c, 5d and 5e on five different planes (called $\beta$ planes), at 0°, 10°, 20°, 30° and 150° respectively.

four other light-cells 7 to insure an auto-calibration of the system by measuring the quantity of light emitted by each lamp and allowing to evaluate (thanks a correct calibration) the illuminance on the lit area 3.

The measurement sequence is the following 1. the first lamp (lamp 2a), at incidence angle 0°, is ON (all three other sources are off).
2. After three second, the 45 light cells placed on the observation arms measure the quantity of light reflected by the road surface.
3. In the meantime, the cells placed beside the light source measure the quantity of light emitted by this one; thanks the calibration of the system, the illuminance on the lit area can than be calculated.
4. The ratio L/E (luminance in a given observation divided by the illuminance on the measured area) can than be calculated.
5. first lamp 2a is off
6. second lamp 2b is ON
7. etc. . . . same cycle with the lamp 2b, 2c and 2d.

If the measured road surface is too bright (more than the clearest road surface type usually seen on the road), the light cells maximum level could be transgressed. The light intensity of the source can than be reduced as necessary, in order to maintain the measured reflected value in the acceptable range (this feature is referred to as the "dimming" feature).

All the values are collected by a laptop type computer using a data acquisition card and specific software.

The system is powered by an integrated battery and is thus entirely independent.

The dimension of the measurement apparatus as represented are: 1020×420×520 mm.

The represented apparatus is designed to provide a system that does not require preheating.

The principle of the comparison analysis method of the measurements can be explained as follows (see also FIG. 1): After having measured the road surface characteristics on site, the collected data (average of the different measurements on a road) are compared to (as many as possible) measurements (realized with the mobile system) stored in a database. By comparing these data, it is then possible by using a "least squares method" to determine the road surface present in the database that presents the closest reflection characteristics to the studied one.

Once this road surface type is determined, the corresponding r-table (as measured using a laboratory type gonio-reflectometer) can be used, with the appropriate lightness coefficient Q0, taking into account a possible resealing factor, in the calculation software in order to predict luminance and uniformity levels.

Of course the accuracy of the method will depend mainly of the size of the database. With the experience of measuring road samples for considerable periods, a database of r-tables which is quite large (more then 500 road samples measured) can be relied on.

Figure 6B:
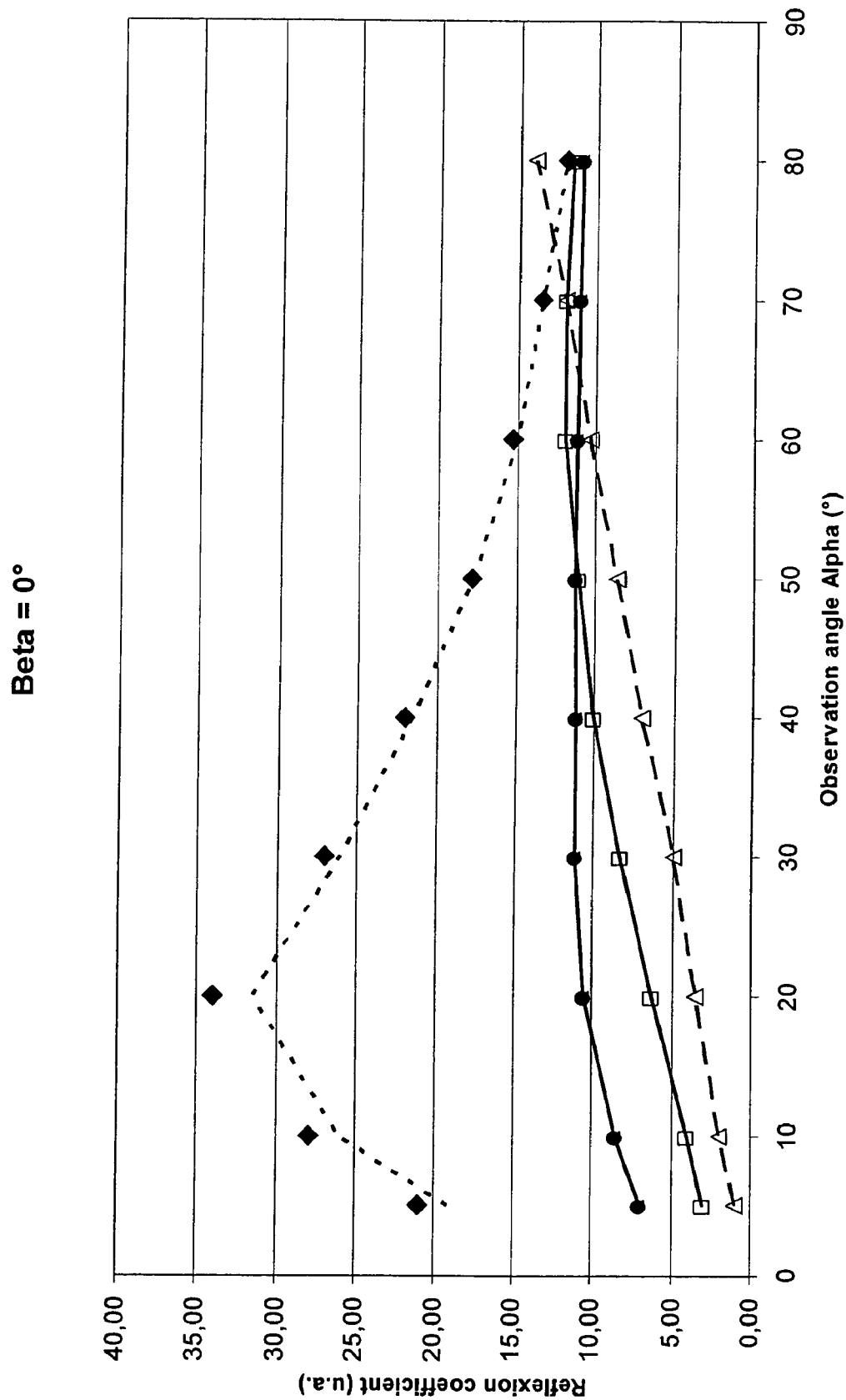
FIG. 6 illustrates angular distribution plots of the relative reflection parameter L/E (as selected light reflection parameter), for the angles ($\gamma$), in function of for the angles ($\alpha$)—respectively ($\beta$)—in view of their comparative analysis by a "least square" method.
Figure 6D:
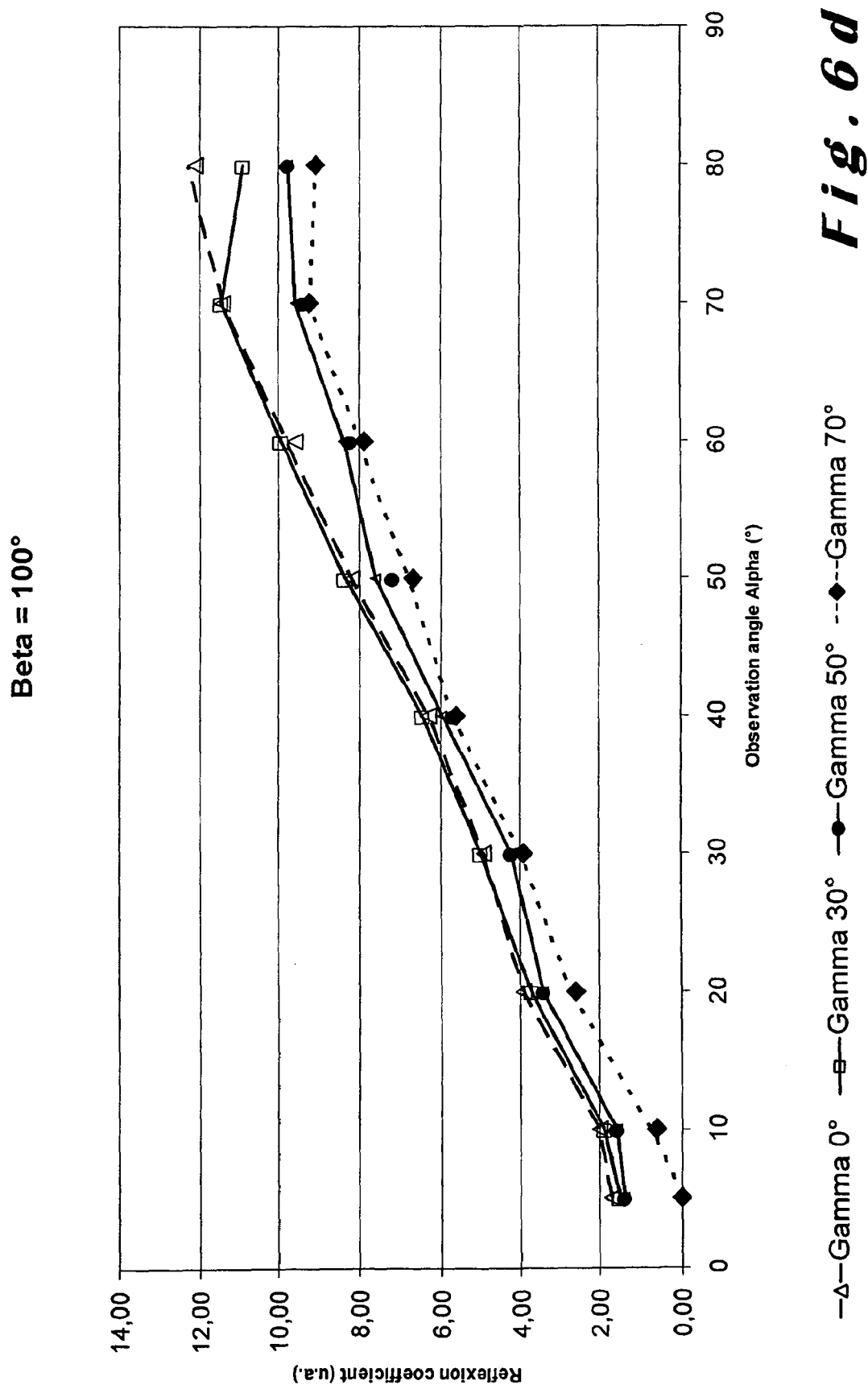
Figure 6E:
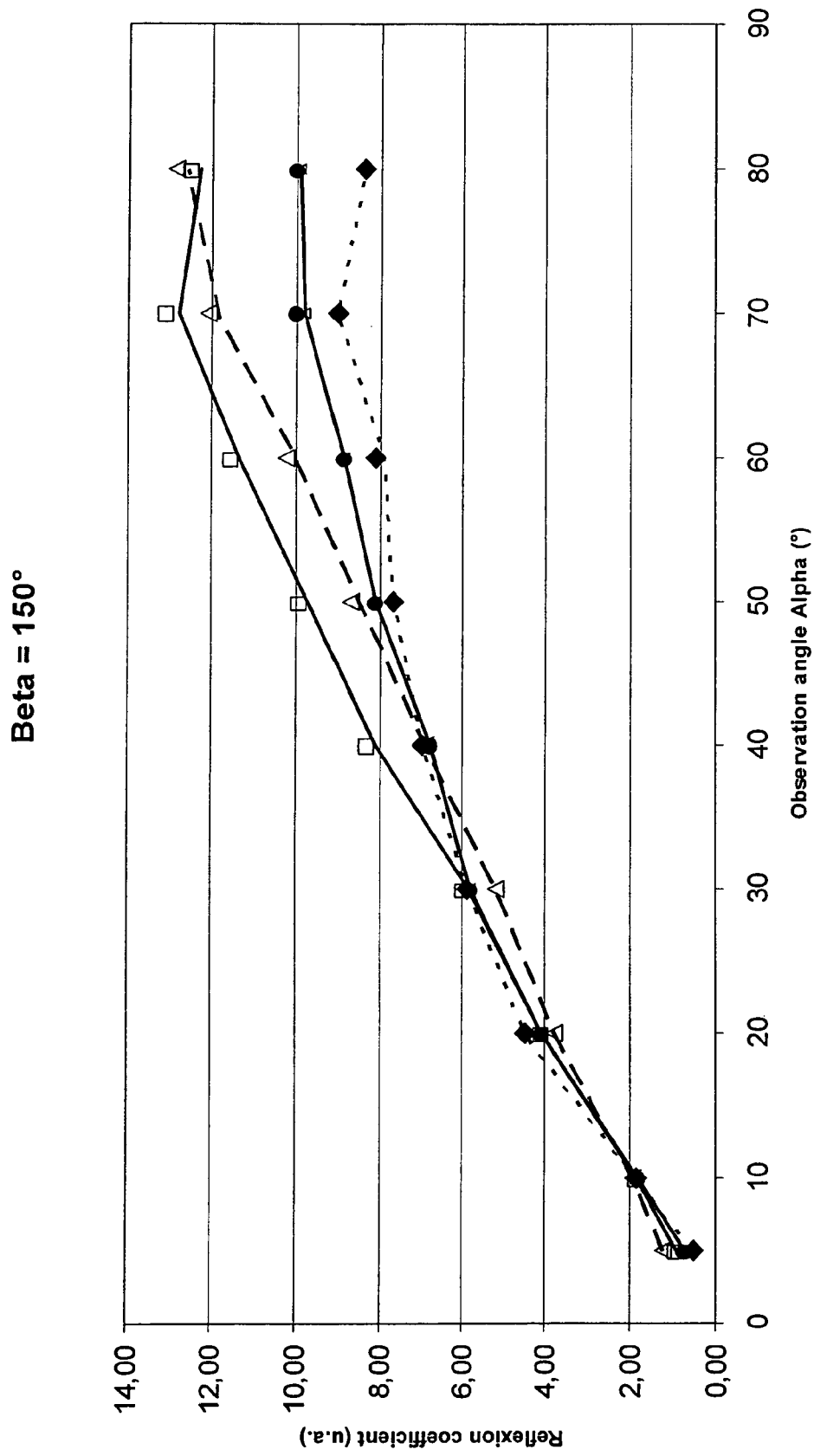

A dedicated software (see also FIG. 6) realizes these comparisons easily and rapidly. It gives a selection of several road surfaces that are the closest in the database, in an order of preference depending on the quality of the correlation.

The invention claimed is:

1. A method for establishing light reflection properties of a specific surface, by selecting from among a number of tables of reduced luminance coefficients (r-tables) measured for comparison surfaces, a table suited to characterise said specific surface, said method comprising:
   a. measuring, for samples of a plurality of comparison surfaces, the parameters for their r-tables, using a measuring apparatus in accordance with CIE standard recommendations;
   b. measuring, for those same samples of a plurality of comparison surfaces, a selected light reflection parameter for a selected combination of angles ($\gamma$) of incident light and angles ($90°-(\alpha)$) and ($\beta$) of reflected light, using a portable measuring apparatus;
   c. measuring in situ, on multiple measuring points of said specific surface, said selected light reflection parameter for said selected combination of angles ($\gamma$) of incident light and angles ($90°-(\alpha)$) and ($\beta$) of reflected light, using said portable apparatus;
   d. comparing, by mathematical and/or graphical analysis, the angular distribution of said selected parameter for the specific surface with the angular distribution of said selected parameter for said comparison surfaces, in order to select the comparison surface showing the best distribution fit, optionally taking into account a rescaling factor on luminance coefficient QO; and,
   e. assigning to said specific surface the light reflection properties of the r-table corresponding to said selected comparison surface, with use of said optional rescaling factor.

2. The method according to claim 1, wherein said at least 60 measurements are carried out for each measured sample/each measuring point, to establish said angular distribution of said selected parameter, involving at least 2 selected angles ($\gamma$), at least 5 selected angles ($\alpha$) and at least 2 selected angles ($\beta$).

3. The method according to claim 2, wherein essentially 180 measurements are carried out, for 4 selected angles ($\gamma$), for 9 selected angles ($\alpha$) and for 5 selected angles ($\beta$).

4. The method according to claim 3, wherein said 180 measurements involve angles ($\gamma$) selected substantially at a 0°, 30°, 50° and 70°, angles ($\alpha$) selected substantially at a 5°, 10°, 20°, 30°, 40°, 50°, 60°, 70° and 80°, and angles ($\beta$) selected substantially at a 0°, 10°, 20°, 30° and 150°.

5. The method according to claim 1, wherein said mathematical comparative analysis of the angular distribution of said selected parameter for the specific surface with the angular distribution of said selected parameter for said comparison surfaces involves a least squares analysis method.

6. The method according to claim 1, wherein said measured light reflection parameter is the measured luminance (L) divided by the measured illuminance (E), whereas said comparative analysis of said angular distributions compares the distributions of L/E in function of angle ($\gamma$), angle ($\alpha$) and angle ($\beta$) respectively.

7. A portable apparatus for measuring light reflection parameters, comprising: a plurality of light sources emitting towards the same region of a surface to be measured, a plurality of reflective light sensors positioned above said region and on either side of and spaced apart from a plane along the axis of said light sources perpendicular to said surface, said apparatus usable in a method for establishing light reflection properties of a specific surface, by selecting from among a number of tables of reduced luminance coefficients (r-tables) measured for comparison surfaces, a table suited to characterise said specific surface, said method comprising:
   a. measuring, for samples of a plurality of comparison surfaces, the parameters for their r-tables, using a measuring apparatus in accordance with CIE standard recommendations;
   b. measuring, for those same samples of a plurality of comparison surfaces, a selected light reflection parameter for a selected combination of angles ($\gamma$) of incident light and angles ($90°-(\alpha)$) and ($\beta$) of reflected light, using a portable measuring apparatus;
   c. measuring in situ, on multiple measuring points of said specific surface, said selected light reflection parameter for said selected combination of angles ($\gamma$) of incident light and angles ($90°-(\alpha)$) and ($\beta$) of reflected light, using said portable apparatus;
   d. comparing, by mathematical and/or graphical analysis, the angular distribution of said selected parameter for the specific surface with the angular distribution of said selected parameter for said comparison surfaces, in order to select the comparison surface showing the best distribution fit, optionally taking into account a rescaling factor on luminance coefficient QO; and,
   e. assigning to said specific surface the light reflection properties of the r-table corresponding to said selected comparison surface, with use of said optional rescaling factor.

8. A method for establishing light reflection properties of a road surface, by selecting from among a number of tables of reduced luminance coefficients (r-tables) measured for comparison surfaces, a table suited to characterise said road surface, said method comprising:
   a. measuring, for samples of a plurality of comparison surfaces, the parameters for their r-tables, using a measuring apparatus in accordance with CIE standard No. 30-2 (TC 4.6) recommendations:
   b. measuring, for those same samples of a plurality of comparison surfaces, a selected light reflection parameter for a selected combination of angles ($\gamma$) of incident light and angles ($90°-(\alpha)$) and ($\beta$) of reflected light, using a portable measuring apparatus;
   c. measuring in situ, on multiple measuring points of said road surface, said selected light reflection parameter for said selected combination of angles ($\gamma$) of incident light and angles ($90°-(\alpha)$) and ($\beta$) of reflected light, using said portable apparatus;
   d. comparing, by mathematical and/or graphical analysis, the angular distribution of said selected parameter for the road surface with the angular distribution of said selected parameter for said comparison surfaces, in order to select the comparison surface showing the best distribution fit, optionally taking into account a rescaling factor on luminance coefficient QO; and,
   e. assigning to said road surface the light reflection properties of the r-table corresponding to said selected comparison surface, with use of said optional rescaling factor.

* * * * *